(12) United States Patent
Ingrisch et al.

(10) Patent No.: US 7,231,807 B2
(45) Date of Patent: Jun. 19, 2007

(54) GAS MEASURING DEVICE AND METHOD WITH COMPENSATION OF DISTURBANCES

(75) Inventors: Kurt Ingrisch, Reutlingen (DE); Markus Niemann, Beckingen (DE); Gerald Hamm, Herrenberg (DE)

(73) Assignee: Paragon AG, Dellbruck (DE)

( * ) Notice: Subject to any disclaimer, the term of this patent is extended or adjusted under 35 U.S.C. 154(b) by 0 days.

(21) Appl. No.: 10/536,608

(22) PCT Filed: Nov. 28, 2003

(86) PCT No.: PCT/DE03/03951

§ 371 (c)(1),
(2), (4) Date: Jan. 30, 2006

(87) PCT Pub. No.: WO2004/051245

PCT Pub. Date: Jun. 17, 2004

(65) Prior Publication Data

US 2006/0155490 A1 Jul. 13, 2006

(30) Foreign Application Priority Data

Nov. 29, 2002 (DE) .................... 102 55 704

(51) Int. Cl.
*G01N 37/00* (2006.01)

(52) U.S. Cl. ...................... 73/23.21
(58) Field of Classification Search ............... 73/23.21
See application file for complete search history.

(56) References Cited

U.S. PATENT DOCUMENTS

| | | | | |
|---|---|---|---|---|
| 2,926,524 A * | 3/1960 | Sanders | ...... | 73/116 |
| 4,155,335 A * | 5/1979 | Hosaka et al. | ...... | 123/676 |
| 4,463,594 A * | 8/1984 | Raff et al. | ...... | 73/23.21 |
| 4,526,147 A * | 7/1985 | Grob | ...... | 123/694 |
| 5,319,921 A * | 6/1994 | Gopp | ...... | 60/274 |
| 6,409,969 B1 * | 6/2002 | Streicher et al. | ...... | 422/94 |
| 7,016,047 B2 * | 3/2006 | May | ...... | 356/480 |
| 2002/0184876 A1 * | 12/2002 | Gopp et al. | ...... | 60/276 |

* cited by examiner

*Primary Examiner*—Michael Cygan
(74) *Attorney, Agent, or Firm*—Andrew Wilford

(57) ABSTRACT

Disclosed is a gas measuring device which comprises compensation of disturbances and offers high accuracy of measurement immediately after being activated. Said gas measuring device is provided with a gas sensor (1) for generating a measuring signal (S1) that depends on the gas concentration and can have a spurious component while a high-pass filter (13) having an adjustable limiting frequency is mounted downstream of said gas sensor (1). The limiting frequency can be predefined according to the spurious component by means of a selection unit.

10 Claims, 2 Drawing Sheets

GAS MEASURING DEVICE AND METHOD WITH COMPENSATION OF DISTURBANCES

CROSS REFERENCE TO RELATED APPLICATIONS

This application is the US national phase of PCT application PCT/DE2003/003951 filed 28 Nov. 2003 with a claim to the priority of German patent application 10255704.7 itself filed 29 Nov. 2002.

FIELD OF THE INVENTION

The invention relates to a gas-measuring device with disturbance or noise compensation and having a gas sensor for generating a measurement signal dependent upon gas concentration and itself having a noise component and a to method with disturbance or noise compensation where a measurement signal dependent upon gas concentration is produced by a gas sensor, the measurement signal including a noise component.

BACKGROUND OF THE INVENTION

For the measurement of gas concentrations and especially the concentrations of carbon monoxide (CO), nitrogen oxides (NO) and hydrocarbons ($C_xH_y$), semiconductor sensors are used in the automotive field because of their low cost. Most of the semiconductor sensors are conductivity-based $SnO_2$ sensors. The measurement results can serve, for example, to open or close air circulation flaps in an automobile.

The above-mentioned sensors are characterized, apart from their low cost, by a good sensitivity to the gases to be measured. On the drawback side, however, these sensors have a number of side effects which complicate the signal evaluation. Reducing gases, like for example carbon monoxide contribute to an increase in the conductivity of the semiconductor sensors. Oxidizing gases like for example nitrogen oxide contribute to a reduction in the conductivity of the semiconductor sensors. In addition, the strong adsorption of water on the surface of the $SnO_2$ semiconductor sensor gives rise to a detrimental side effect. The bound water increases the conductivity of the gas-sensitive $SnO_2$ layer significantly. The amount of water adsorbed on the sensitive $SnO_2$ layer is dependent to a high degree upon the temperature. As a result the change in the conductivity of the $SnO_2$-layer is strongly temperature dependent. At a temperature below 200° C. substantially greater quantities of water can be bound to the semiconductor sensors than at higher temperatures. The adsorbed water quantities can be determined by means of a TDS [Total Dissolved Solids] measurement. After a certain time, a temperature-dependent equilibrium develops between adsorbed and desorbed water. Upon a change in temperature, the time constant to reach a new equilibrium is between several minutes and several hours. The time constant depends upon prevalent environmental conditions.

This effect arises especially in the phase following the switching on of the semiconductor sensor or in operation and is especially detrimental in its manifestations.

If the sensor is stored at ambient temperature for a period of several weeks, in the course of this period there will be an equilibrium for this temperature at saturation between adsorbed water and desorbed water. This equilibrium is referred to hereinafter also as the saturation equilibrium. To be able to carry out gas measurements with the sensor, the sensor is brought to an operating temperature of about 330° C. The increased temperature of 330° C. by contrast with the storage temperature means that water will be desorbed until a new saturation equilibrium is formed. During this period of time, as a consequence, the conductivity will drop continuously even if the gas concentration should remain constant. The resulting drop in conductivity is correlated with a conductivity change of the type which can result from a large increase in the NO concentration.

The result is that the measurement of the NO concentration during the interval in which a new saturation equilibrium is created is associated with significant errors in measurement.

OBJECT OF THE INVENTION

It is therefore an object of the present invention to provide an improved noise-suppressing gas sensor

SUMMARY OF THE INVENTION

The gas-measuring device according to the invention with disturbance or noise compensation has, by comparison with the state of the art, the advantage of a high measurement precision rapidly following the initiation of operation of the gas-measuring device, that is after it has been switched on. This is achieved in that the gas-measuring device with noise compensation encompasses a gas sensor for generating a gas concentration dependent measurement signal which can include a noise component. The gas sensor is followed by a high-pass filter with an adjustable pass or limiting frequency. The limiting frequency is selected or predetermined by means of a selector unit as a function of the noise component.

The method according to the invention for gas measurement with noise compensation has, by comparison with the state of the art, the advantage that the measurement can be effected already directly following the switching on of the gas-measuring device with high precision. The method thus involves the following steps: By means of a gas sensor, a measurement signal is generated with a measurement signal dependent upon the gas concentration and which can have a noise component. Then the measurement signal is filtered by means of a high-pass filter with an adjustable pass or limiting frequency, whereby the limiting frequency can be selected by a selection unit dependent upon the noise component or predetermined by the noise component.

Thus in one feature of the invention, a low-pass filter is provided which is located between the evaluating unit and the gas sensor.

In a further feature of the invention, a computing unit is provided between the evaluating unit and the low-pass filter. The computing unit is provided for calculating the pitch or slope of the filter output signal obtained from the low-pass filter.

In an additional feature of the invention, the selector unit is connected at its output side with a control input of the high-pass filter and is so configured that with it, based upon the pitch or slope of the filter output signal, a value can be selected with which the limiting frequency of the high-pass filter can be adjusted.

In an embodiment of the gas-measuring device according to the invention, the selector unit is so configured that a first filter value is predetermined therewith when the difference between the sensor value and a set-point value exceeds a limiting value. A second filter value can also be predeterminable when the difference between the set-point value and the sensor value lies within a predetermined range. Finally a third filter value can be predeterminable when the sensor value corresponds to the set-point value.

In a further embodiment of the gas-measuring device according to the invention, the first, the second and the third filter values can be respective time constants.

Advantageously, the gas-measuring device according to the invention can have a comparator in circuit with the high-pass filter but downstream thereof. With this comparator, the filter signal can be compared with a threshold value.

In another feature of the gas-measuring device according to the invention, the gas sensor is an $SnO_2$ gas sensor.

Finally in a further embodiment of the gas-measuring device of the invention, the gas sensor can be so configured that nitrogen oxide is measurable therewith.

BRIEF DESCRIPTION OF THE DRAWING

In the following, the invention will be further described based upon three figures.

MODE OF CARRYING OUT THE INVENTION

Figure 1:
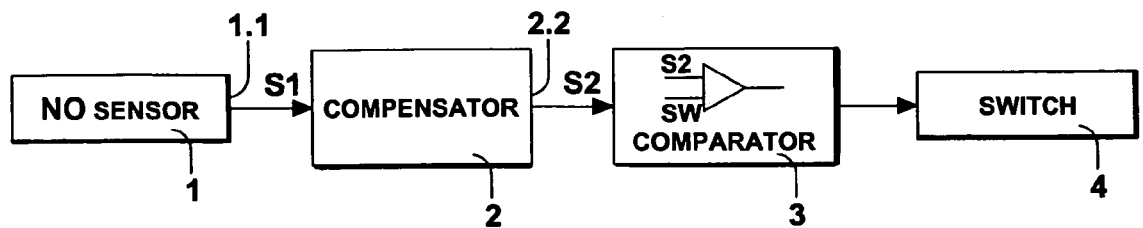
FIG. 1 shows by way of a signal flow diagram, the principal approaches to compensation of the disturbance or noise.

In FIG. 1 the basic course of the signal flow of the measuring device has been shown. An NO sensor 1 supplies at its output 1.1, referred to also as the sensor output below, a sensor signal S1 which, aside from the measured gas concentration, also includes a noise component which can represent a shift in the saturation equilibrium. The sensor signal S1 is evaluated with an inlet compensation 2 determining whether a noise signal component resulting from desorption is present and, optionally, how high this noise signal component is. Optionally the noise signal component is compensated in the sensor signal S1.

At the output of the single channel compensation 2.2, a sensor signal S2 is obtained which has been freed from the noise signal component and which is compared with a threshold value. For that purpose a threshold evaluation 3 is provided. At the end, a control signal is obtained in the form of a switching signal 4 which controls the air circulation flaps not shown in the figures.

Figure 2:
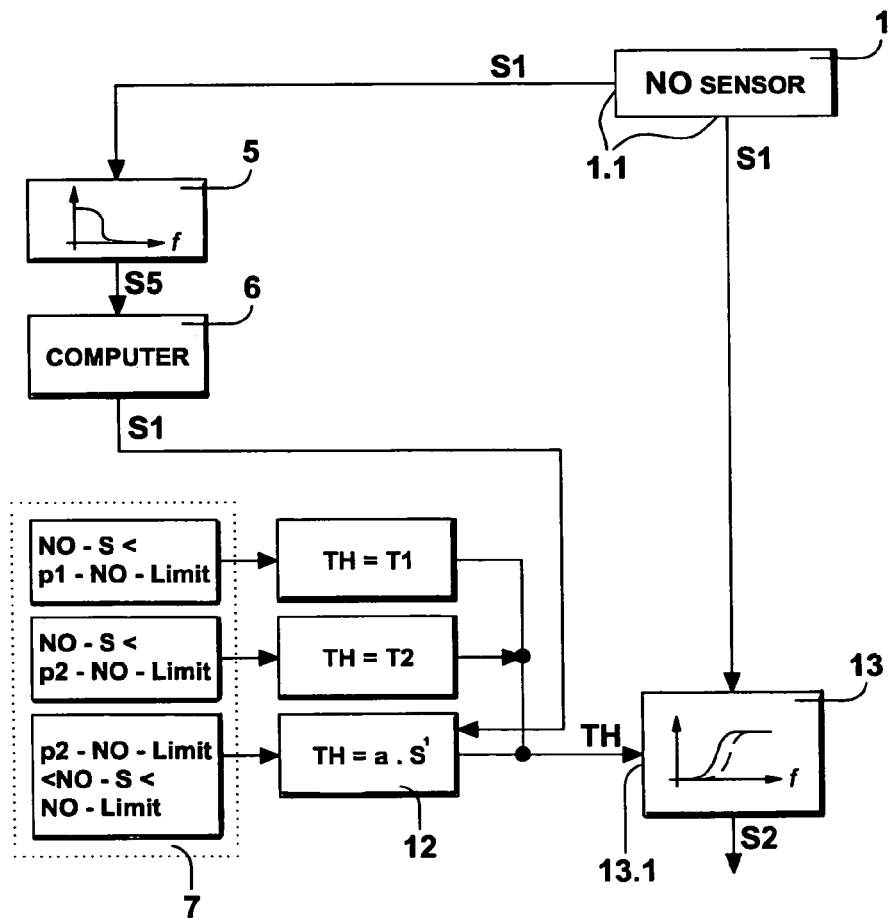
FIG. 2 shows in the form of a block diagram the main components of the gas-measuring device of the invention.

The configuration of the single channel or inlet compensation 2 has been represented in FIG. 2 in the form of a further block diagram. The NO sensor 1 is connected at its output side with a low-pass filter 5 which filters the sensor signal S1. The low-pass filter 5 has a time constant tv. At the output of the low-pass filter 5 a filtered sensor signal (S5) is present. The filter sensor signal S5 is further processed by means of a computer unit 6. With this circuit, from the filter sensor signal S5, a pitch or Slope S' is calculated. Then the pitch or slope S' is fed to a unit 12 having a time constant THE. The unit 12, generating the time constant THE, calculates it from the slope S' and a parameter a. If the sensor signal S1 of the NO sensor 1 has a time calculated for it which corresponds to the time constant in normal operation, this signal is fed to the high-pass filter 13 via its control input 13. This is the case when the conductivity value NO-S of the sensor 1 lies between a p2' NO limit and the NO limit. This is predetermined by means of a decision [logic] circuit or unit 7.

If the decision unit or circuit 7 determines that the difference between the actual conductivity value of the NO sensor 1 and the limiting value, the NO limit, is too great, that is that the conductivity value NO-S of the sensor 1 is smaller than p1' NO limit, at the control input 13.1 of the high-pass filter 13 the time constant THE=T1 will be applied. This is the case exclusively at the beginning of the initial operation of the sensor 1.

In this case one can reckon on a large slope S' of the sensor signal S1.

Since, when the sensor 1 is placed in operation, no data as to the course of the signal S1 until saturation equilibrium is reached is available, depending upon the difference between the conductivity value of the NO sensor 1 and the limiting value NO limit, a fixed limiting frequency which is obtained from experience is used at start up. The values are derived from a table which has been designated below as a "look-up" table. The table values are those when may be obtained under start up conditions as a function of the actual differences. T1 and T2 are matched to the system requirements.

In case the difference between the actual conductivity value of the NO sensor 2 the limiting value NO limit is small, that is the conductivity value NO-S of the sensor 1 is smaller than the P2' NO limit, the time constant THE=T2 is applied to the control input 13.1 of the height pass filter 13. From the slope S' of the filter signal sensor S5, the noise amplitude of the signal S2 following the high-pass filter 13 can be estimated. The time constant THE for the high-pass filter 13 is so selected that a defined limited noise amplitude of the signal S2 arises at the output of the high-pass filter 13. The noise amplitude is so selected that a circulation flap controllable with the signal S2 will not be inadvertently closed.

The start up process for the sensor 1 is a monotonic process which terminates when the saturation equalizes, that is the equilibrium between absorption and desorption of water at the NO sensor 1 has been reached.

The signal shape of the logarithmic resistance Inc can be determined to a first approximation from the point in time at which the sensor is switched on by the function $$Inc = a \cdot \left(1 - e^{\frac{t}{T}}\right) + b$$

in which t is the time, a is an experimental parameter and represents a transfer or translation factor between the pitch S' and the limiting frequency, b is an experimental parameter and T is an experimental parameter.

The measured signal has a useful signal component and a noise component, the latter of which is determined by the desorption of water and has the characteristics of a PT1 step function.

By PT1 a time delay element of the first order is to be understood. In the frequency spectrum this step function prevails until a higher frequency component begins which decreases with increasing time and ultimately disappears.

The noise signal component, described below also as the noise or disturbance signal which is a function of the desorption of water, is suppressed from the beginning by the high-pass filter 13 with a limiting frequency selected to be suitably high for a predetermined time interval. With progress of the running in process the high frequency component in the noise signal decreases. This is taken into consideration in the calculation by a continuous reduction of the limiting frequency of the high-pass filter 13. As soon as an equilibrium is reached between absorption and desorption, the limiting frequency of the high-pass filter 13 remains constant and the measurement signal which at the start was damped and which thereafter consists of the purely usable signal, is completely available for control purposes. The signal obtained at the output of the high-pass filter 13 then serves to control the air-circulating flaps. To match the limiting frequency for the high-pass filter 13 dynamically, during the start up phase of the NO sensor 1 an approximation technique is used.

After longer operation of the NO sensor 1 without the use of the latter for the measurement of gas, the conductivity results which is indicated by the NO limit. The NO limit conductivity thus corresponds to an equilibrium between desorption and adsorption at the operating temperature of the NO sensor 1. In practice however the case in which the NO sensor 1 is not used for the measurement of gas hardly ever arises. As a consequence, the value of the conductivity upon attainment of the equilibrium must be determined approximately in that the sensor signal S1 must be filtered by means of the low-pass filter 5. The time constant tv is here about 30 seconds. The conductivity value thus obtained is retained in operation in a nonvolatile memory.

The pitch S' of the sensor signal S1 is, shortly after the NO sensor 1 is placed in operation, as noted, highly dependent upon the storage time for the NO sensor 1. The storage duration can be taken into consideration by the control unit, however, only at high cost. As an alternative, one can observe the sensor signal S1 for a certain time after the sensor 1 has been turned on and then switch over to a further course of the sensor signal S1. To minimize the effect of higher gas concentrations for short intervals, the sensor signal S1 is initially filtered by means of the low-pass filter 5 and then its pitch S' is determined.

The amplitude of the noise signal component resulting form the shift in the equilibrium, falls monotonically in the course of the start up process.

The experimental parameters a, b and T depend upon the storage time of the sensor 1 and upon the sensor 1. These parameters cannot be determined experimentally and are obtained from the start up compensation.

With the invention, the different signal dynamics between a signal variation produced during gas measurement and the signal changes resulting from desorption of water are utilized.

A change in the concentration of the gases to be measured usually has a time constant between 2 and 30 seconds. The noise signal which is a function of the desorption of water after a prior storage of the sensor for a period of time, can have a time constant between a few minutes and several hours.

Figure 3:
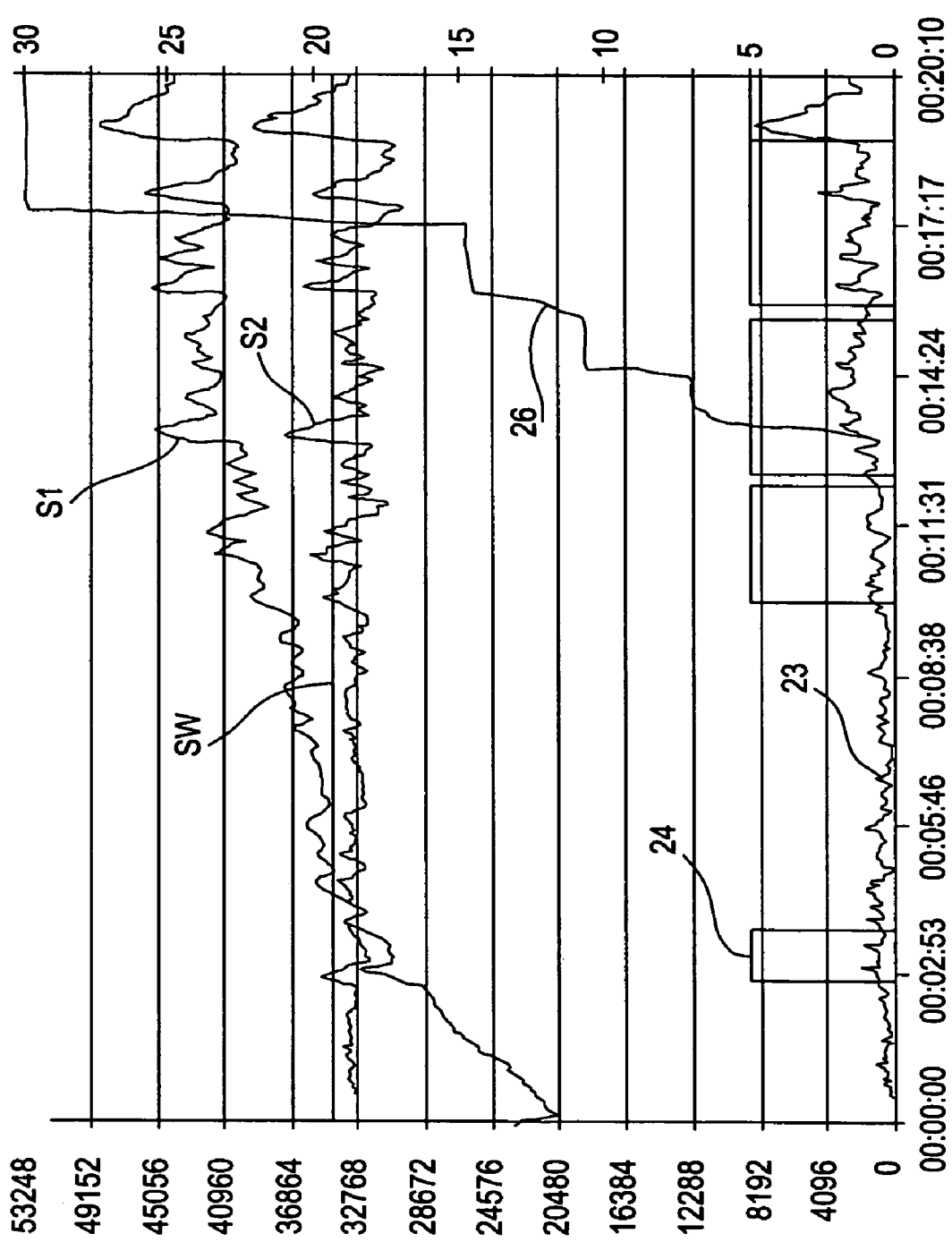
FIG. 3 shows the course of a number of signals as may arise.

In FIG. 3, timing diagrams of a number of signal courses have been shown. Time appears along the x-axis and the amplitude is given along the y-axis of the diagrams. It can be noted that the amplitude of the non compensated NO sensor signal S1 is strongly increased at the start and later only increases to a slight extent.

The course of the compensate sensor signal is also indicated in FIG. 3 and is provided at the reference character S2.

The threshold value SW, the filter signal 23, the control signal 24 for the circulator flap and the time constant 26 are also indicated in FIG. 3. From the increasing time constant 26, it can be seen how the limiting frequency of the HP filter is adjusted toward lower values and the system thus becomes more sensitive to gas pulses.

The invention claimed is:

1. A gas-measuring device with noise compensation having a gas sensor for generating a measurement signal dependent upon gas concentration and which includes a noise component, characterized in that the gas sensor has connected downstream thereof a high-pass filter with an adjustable limiting frequency predeterminable by means of an evaluating unit as a function of the noise component.

2. The gas-measuring device according to patent claim 1 characterized in that a low-pass filter is provided connected between the evaluating unit and the gas sensor.

3. The gas-measuring device according to patent claim 2, characterized in that a computing unit is connected between the evaluating unit and the low-pass filter and is provided for calculating a pitch of the filter output signal arising from the low-pass filter 5.

4. The gas-measuring device according to patent claim 1, characterized in that the evaluating unit at its output side is connected with a control input of the high-pass filter and is so configured that with it, based upon the pitch of the filter output signal a value can be selected with which a limiting frequency of the high-pass filter 13 is adjustable.

5. The gas-measuring device according to claim 1 characterized in that the evaluating unit is so configured that with it a first filter value can be predetermined when a difference between the sensor value and a set point exceeds a limiting value, so that a second filter value is predetermined when the difference between the sensor value and the set point value lies within a certain range, and a third filter value is predetermined when the sensor value corresponds to the set-point value.

6. The gas-measuring device according to patent claim 5 characterizing in that the first, second, and third filter values are time constants.

7. The gas-measuring device according to claim 1, characterized in that the high-pass filter has a comparator connected downstream thereof.

8. The gas-measuring device according to claim 1, characterized in that the gas sensor is an $SnO_2$ gas sensor.

9. The gas sensor according to claim 1, characterized in that the gas sensor is so configured that nitrogen oxide is measurable therewith.

10. A method of gas measurement with noise compensation, whereby a measurement signal dependent upon gas concentration is produced by a gas sensor and the measurement signal can include a noise component, characterized in that the measurement signal is filtered by means of a high-pass filter with an adjustable limiting frequency, whereby the limiting frequency is selectable by a evaluating unit as a function of the noise component.

* * * * *